United States Patent [19]
Endo et al.

[11] Patent Number: 5,705,382
[45] Date of Patent: Jan. 6, 1998

[54] METHOD FOR PRESERVING NITRILE HYDRATASE OR NITRILASE ACTIVITY OF MICROBIAL CELLS WITH INORGANIC SALTS

[75] Inventors: Takakazu Endo; Toshiaki Doi; Koji Tamura; Yuji Hirata; Kouzo Murao, all of Kanagawa, Japan

[73] Assignee: Nitto Chemical Industry Co., Ltd., Tokyo, Japan

[21] Appl. No.: 542,291

[22] Filed: Oct. 12, 1995

[30] Foreign Application Priority Data

Oct. 14, 1994 [JP] Japan ............... 6-274241

[51] Int. Cl.$^6$ ............... C12N 1/04; C12N 11/04; C12N 9/96; C12N 1/12
[52] U.S. Cl. ............... 435/260; 435/174; 435/177; 435/182; 435/188; 435/252.1
[58] Field of Search ............... 435/174, 176, 435/177, 178, 180, 182, 188, 260

[56] References Cited

U.S. PATENT DOCUMENTS

| | | | |
|---|---|---|---|
| 4,900,672 | 2/1990 | Yamada et al. | 435/188 |
| 5,326,702 | 7/1994 | Endo et al. | 435/129 |
| 5,334,519 | 8/1994 | Yamada et al. | 435/129 |

FOREIGN PATENT DOCUMENTS

| | | |
|---|---|---|
| 0496001A1 | 7/1992 | European Pat. Off. |
| 0610048A2 | 10/1994 | European Pat. Off. |
| 0666320A2 | 9/1995 | European Pat. Off. |

OTHER PUBLICATIONS

Ichihara et al., "A Manganese and Iron–Containing Superoxide Dismutase from *Rhodococcus Bronchialis*", *J. Gen. Appl. Microbiol.*, 26:387–393, (1980).

Kastner et al., "Enumeration and Characterization of the Soil Microflora from Hydrocarbon–contaminated Soil Sites Able to Mineralize Polycyclic Aromatic Hydrocarbons (PAH)", *Appl. Microbiol. Biotechnol.*, 41:267–273, (1994).

*Primary Examiner*—David M. Naff
*Attorney, Agent, or Firm*—Sughrue, Mion, Zinn, Macpeak & Seas, PLLC

[57] ABSTRACT

Cells having enzyme activity, and the enzyme activity thereof, are preserved for a prolonged period of time, as a suspension of microbial cells or as a suspension of immobilized cells in particles, in an aqueous medium that is a neutral or weakly basic aqueous solution of inorganic salts, having a molarity ranging from 100 mM to the saturation concentration of the inorganic salts. Preferably, the microbial cells are cells containing the enzyme, nitrile hydratase or nitrilase, such as *Gordona terrae* or *Rhodococcus rhodochrous*, and the inorganic salts are phosphates, borates, sulfates, sulfites or hydrochlorides. The present invention provides an industrially useful method for preserving a large quantity of cells or immobilized cells in particles having nitrile hydratase or nitrilase enzyme activity for a prolonged period of time (e.g., 300 days) without cell lysis or enzyme deterioration even at room temperature. The present invention also renders possible a sharp reduction in labor and cooling cost, which are necessary in the conventional preservation process.

13 Claims, No Drawings

METHOD FOR PRESERVING NITRILE HYDRATASE OR NITRILASE ACTIVITY OF MICROBIAL CELLS WITH INORGANIC SALTS

FIELD OF THE INVENTION

This invention relates to a method for preserving a suspension of cells or immobilized cells. More particularly, this invention relates to a method in which microbial cells produced by culturing or immobilized cells thereof are stably preserved as a suspension in an aqueous medium.

BACKGROUND OF THE INVENTION

Enzymes produced by microorganisms are used in many fields as catalysts of chemical conversion reactions. In particular, nitrile hydratase and nitrilase are capable of hydrating or hydrolyzing nitrile groups, which allows low cost production of amides, carboxylic acids and α-hydroxycarboxylic acids, which are important in the field of industrial chemistry. In addition, said enzymes are capable of optically specific hydration or hydrolyzation, which allows production of optically active carboxylic acids, amino acids and α-hydroxycarboxylic acids, which are important production materials for medicines and agricultural chemicals.

In a chemical conversion reaction, in which a microbial enzyme is used as a catalyst, cultured and collected microbial cells or immobilized cells thereof must be stably preserved until their use. That is, it is necessary to store them under such conditions that the catalytic function of the enzyme is preserved, and the cells do not putrefy or lyse due to microbial contamination. In consequence, inactivation of enzymes and lysis and putrefaction of cells are generally prevented by freezing or refrigeration.

Among the preservation methods known to date, freezing microbial cells or immobilized cells in particles requires complex freezing and thawing steps, which can also result in distroyed or reduced enzyme activity. The refrigeration preservation method requires relatively low preservation temperatures to prevent microbial contamination and to stabilize the cells, thus entailing high cooling costs.

SUMMARY OF THE INVENTION

Intensive studies on inexpensive and stable preservation conditions for cultured and collected cells or immobilized cells thereof have been conducted. As a result, the inventors have found that such cells or immobilized cells thereof can be stably preserved for 300 days or more, without causing cell lysis or enzyme inactivation, even at room temperature, when they are preserved in a neutral to basic aqueous solution of inorganic salts, having a molarity ranging from 100 mM to the saturation concentration of the inorganic salts. The present invention has been accomplished on the basis of this finding.

Thus, the present invention provides a method for preserving a suspension of microbial cells or immobilized cells thereof, in which the microbial cells having enzyme activity and the enzyme activity thereof are stably preserved for a prolonged period of time as a suspension of the microbial cells or as a suspension of the cells immobilized in particles in an aqueous medium, wherein the aqueous medium is a neutral or weakly basic aqueous solution having a molarity ranging from 100 mM to the saturation concentration of the inorganic salts.

Other objects and advantages of the present invention will be apparent from the following description of the invention.

DETAILED DESCRIPTION OF THE INVENTION

The aqueous solution of inorganic salts of the present invention is an aqueous solution of at least one salt selected from the group consisting of phosphates, borates, sulfates, sulfites and hydrochlorides; and the phosphate or borate aqueous solution may preferably be in the form of a phosphate or borate buffer. Types of the salts include sodium salts, potassium salts and ammonium salts.

The aqueous solution of inorganic salts of the present invention is a highly concentrated aqueous solution, having a molarity ranging of from 100 mM to the saturation concentration of the inorganic salt. The saturation concentration varies depending on each salt and the temperature, and is preferably within the range of from 300 to 500 mM.

Also, the aqueous solution of inorganic salts should be neutral to basic and is generally adjusted to a pH value of from pH 7 to 10, preferably from pH 7.5 to 9.5.

The enzyme and the microorganism having the enzyme activity are not particularly limited. Examples of the enzyme include nitrile hydratase, nitrilase and the like.

Although a number of microorganisms are known as to produce nitrile hydratase and nitrilase, microorganisms belonging to the genera Rhodococcus and Gordona are preferred because of their high enzyme activities.

Illustrative examples of such microorganisms include Rhodococcus sp. HT40-6 (FERM BP-5231), Rhodococcus rhodochrous ATCC 33278, Rhodococcus rhodochrous J-1 (FERM BP-1478) and Gordona terrae MA-1 (FERM BP-4535).

Of these strains, Rhodococcus rhodochrous ATCC 33278 is a known strain and can be obtained easily from the American Type Culture Collection (ATCC). Also, Rhodococcus sp. HT40-6 and Rhodococcus rhodochrous J-1 are known strains that are deposited at the National Institute of Bioscience and Human Technology (formerly, Fermentation Research Institute), Agency of Industrial Science and Technology, at 1–3, Higashi 1-chome, Tsukuba-shi, Ibaraki-ken, 305, Japan, under the aforementioned designations, and their bacteriological properties are described, respectively, in JP-A-4-222591 and JP-B-6-55148 (the terms "JP-A" and "JP-B" as used herein mean an "unexamined published Japanese patent application" and an "examined Japanese patent publication", respectively).

Gordona terrae MA-1 is a strain isolated from soil by some of the present inventors and is deposited under Accession No. FERM BP-4535 in the National Institute of Bioscience and Human Technology, Agency of Industrial Science and Technology Tsukuba-shi, Ibarakiken, JAPAN, under the aforementioned designation. The bacteriological properties of this strain are as follows.

| Strain MA-1 | |
| --- | --- |
| Morphology | polymorphic rod |
| Gram-stain | + |
| Spore | − |
| Motility | − |
| Oxidase | − |
| Catalase | + |
| Color of colony | pink to orange |
| Rod-coccus cycle | + |
| Elongation of peripheral cells of colony | yes |
| Formation of aerial hypha | no |
| Behavior against oxygen | aerobic |

-continued

| Strain MA-1 | |
|---|---|
| Diamino acid in cell wall | meso-diaminopimelic acid |
| Glycolyl test | + (glycolyl type) |
| Sugar composition of cell wall | |
| arabinose | + |
| galactose | + |
| Quinone system | MK-9 (H$_2$) |
| Adenine hydrolysis | − |
| Tyrosine hydrolysis | − |
| Urea hydrolysis | + |
| Assimilation | |
| inositol | − |
| maltose | − |
| mannitol | + |
| rhamnose | + |
| sorbitol | + |
| sodium m-hydroxybenzoate | − |
| sodium benzoate | + |
| sodium citrate | + |
| sodium lactate | + |
| testosterone | + |
| acetamide | − |
| sodium pyruvate | + |
| Growth in the presence of 0.02% sodium azide | + |
| Growth at 10° C. | + |
| Growth at 40° C. | + |
| Growth in the presence of 0.001% crystal violet | + |
| Growth in the presence of 0.3% phenylethanol | + |
| Growth in the presence of 5% NaCl | + |
| Growth in the presence of 7% NaCl | + |

When these bacteriological properties were classified based on Bergey's Manual of Systematic Bacteriology (1986); J. Gen. appl. Micribiol., 34, 341–348 (1988) and Int. J. Syst. Bacteriol., 39, 371 (1989), the strain MA-1 was identified as a bacterium belonging to the species Gordona terrae.

Next, general aspects of the present invention are described.

The microorganism used in the present invention is cultured by using a medium containing assimilable carbon sources (such as glucose and fructose), nitrogen sources (such as yeast extract, peptone and ammonium sulfate) and inorganic salts (such as magnesium chloride, ferric chloride, and disodium hydrogen phosphate), as well as metal salts to be used as prosthetic groups necessary for the induction of nitrile hydratase and nitrilase activities (such as cobalt chloride and ferric sulfate), and nitriles (such as benzonitrile, isobutyronitrile and succinonitrile) and amides (such as ε-caprolactam, isobutylamide and propionamide) to be used as inducers. Culturing may be carried out at a medium pH of from pH 4 to 10, preferably from pH 6 to 9 and at a culture temperature of from 20° to 40° C., preferably from 25° to 35° C., for 1 to 7 days, until the enzyme of interest reaches its maximum activity.

The resulting cells are collected by centrifugation and washed once or twice with a borate or phosphate buffer. Thereafter, the cell suspension is mixed with the aforementioned aqueous solution of inorganic salts in such an amount that the final concentration of interest is obtained.

When the cells are used in an immobilized form, a suspension of washed cells is immobilized and then granulated in the following manner. That is, a mixture of at least one acrylic monomer (for example, acrylamide, acrylic acid, methacrylamide, methacrylic acid, N,N-dimethylacrylamide, N,N-diethylacrylamide, dimethylaminopropyl acrylate, dimethylaminopropyl methacrylate dimethylaminopropyl acrylamide, dimethylaminopropyl methacrylamide, diethylaminopropyl acrylamide or diethylaminopropyl methacrylamide) and a crosslinking agent (for example, methylene bisacrylamide, methylene bismethacrylamide, 1,2-dihydroxyethylene bisacrylamide or bisacrylamidoacetic acid) is added to a suspension of washed cells, and then a polymerization initiator and accelerator (such as ammonium persulfate and N,N,N',N'-tetramethylethylenediamine) are added to the resulting suspension to cause polymerization and gelation. Thereafter, the thus obtained gel is cut into particles, generally cubes of about 0.5–100 mm square, which are washed with a borate or phosphate buffer, and then mixed with the aqueous solution of inorganic salts in the same manner as described above in regard to a suspension of cells.

In the immobilization step, generally 0.1 to 40% by weight, preferably 1 to 20% by weight, of the cells on a dry weight basis are mixed with generally 2 to 30% by weight, preferably 5 to 15% by weight, of the monomer mixture.

Though not particularly limited, the concentration of preserved cells or immobilized cells in particles may be within the range of from 0.1 to 30% by weight on a dry cell basis.

The preservation temperature is generally from 0° to 40° C., preferably from 0° to 35° C.

In order to prevent putrefaction during cell preservation, a drug may be added to the preservation solution that has an antibacterial or antifungal activity, and other salts, such as of ethylenediaminetetraacetic acid, may be added.

When the thus preserved cells or immobilized cells in particles are used in a production reaction as a conversion catalyst, the cell suspension may be added to the reaction solution directly or after washing, as the occasion demands.

The following examples are provided to further the present invention. It is to be understood, however, that the examples are for illustration only and are not intended as a definition of the limits of the present invention. All the percentages are by weight unless otherwise indicated.

INVENTIVE EXAMPLE 1

(1) Culturing

Gordona terrae MA-1, which has nitrilase activity, was cultured aerobically at 30° C. for 72 hours in the following medium supplemented with 1-cyclohexenylacetonitrile as an enzyme activity inducer.

| Medium composition (pH 7.5): | |
|---|---|
| Glucose | 30 g |
| Sodium glutamate | 15 g |
| Yeast extract | 8 g |
| Disodium hydrogen phosphate | 7.1 g |
| Potassium dihydrogen phosphate | 6.8 g |
| Sodium sulfate | 2.8 g |
| Magnesium chloride | 0.4 g |
| Calcium chloride | 0.04 g |
| Manganese sulfate | 0.03 g |
| Iron chloride | 0.006 g |
| Zinc sulfate | 0.003 g |
| 1-Cyclohexenylacetonitrile | 0.5 g |
| Distilled water | 1,000 ml |

(2) Preparation of Cell Suspension to be Preserved

The cultured broth was dispensed in 45 ml portions in centrifugation tubes and centrifuged (10,000 rpm, 15 minutes, 10° C.), and the thus collected cells in each tube were washed once with 45 ml of 50 (comparative example), 100, 300, 500 or 700 mM phosphate buffer (pH 8.0, $K_2HPO_4$—$KH_2PO_4$) and again suspended in 45 ml of the respective concentration of phosphate buffer used in the wash. Each cell suspension was dispensed in 15 ml portions into 3 capped glass containers and preserved in the dark at 5, 20 or 30° C. After 0, 120 or 300 days of preservation, a portion of each cell suspension was sampled to measure the enzyme activity.

(3) Measurement of Nitrilase Activity

A small portion of each preserved cell suspension was subjected to centrifugation (1,500 rpm, 5 minutes, 10° C.), and the thus collected cells were washed twice with 2 volumes of 50 mM phosphate buffer (pH 8.0, $Na_2HPO_4$—$KH_2PO_4$) and suspended in the same phosphate buffer, further supplemented with 100 mM sodium sulfite. Nitrilase activity was determined by adding 20 mM of mandelonitrile as the substrate to the cell suspension and, after 30 minutes of shaking at 30° C., the cells were removed by centrifugation (1,500 rpm, 5 minutes, 10° C.). The amount of R-mandelic acid contained in the resulting supernatant fluid was analyzed by liquid chromatography (column, Wakosil ODS 5C18; eluent, 0.1M phosphoric acid:acetonitrile=3:1; detection wave length, 254 nm).

One unit (1 U) of enzyme activity was defined as the capacity of 1 mg of dry cells to produce 1 μmol of mandelic acid per 1 minute in 1 ml of the reaction solution. The amount of enzyme activity in 1 ml of reserved cell suspension was calculated by multiplying the activity of 1 mg of dry cells by the amount of dry cells (mg) in 1 ml of the preserved cell suspension.

(4) Results

Table 1 shows relative enzyme activity values, with the activity in 1 ml of each preserved cell suspension on day 0 day defined as 1.0.

TABLE 1

| Concentration of phosphate buffer (mM) | Preservation Temperature (°C.) | | | | | | | | |
|---|---|---|---|---|---|---|---|---|---|
| | 5 | | | 20 | | | 30 | | |
| | Days Preserved | | | | | | | | |
| | 0 | 120 | 300 | 0 | 120 | 300 | 0 | 120 | 300 |
| 50 | 1.0 | 0.4 | 0.0 | 1.0 | 0.0 | 0.0 | 1.0 | 0.0 | 0.0 |
| 100 | 1.0 | 1.0 | 0.8 | 1.0 | 0.8 | 0.5 | 1.0 | 0.7 | 0.3 |
| 300 | 1.0 | 0.9 | 0.9 | 1.0 | 1.1 | 0.9 | 1.0 | 0.9 | 0.6 |
| 500 | 1.0 | 1.2 | 1.1 | 1.0 | 1.2 | 0.9 | 1.0 | 0.9 | 0.9 |
| 700 | 1.0 | 1.1 | 1.1 | 1.0 | 1.1 | 0.9 | 1.0 | 0.9 | 0.9 |

INVENTIVE EXAMPLE 2

The cultured broth of Inventive Example 1 was dispensed in 20 ml portions in 6 centrifugation tubes and centrifuged (10,000 rpm, 15 minutes, 10° C.), and the thus collected cells in each tube were washed once with the same volume of 50 mM phosphate buffer (pH 8.0, $K_2HPO_4$—$KH_2PO_4$) and resuspended in 20 ml of the above 50 mM phosphate buffer, further supplemented with 300 mM sodium sulfate, 300 mM sodium chloride, 300 mM potassium chloride or 100 mM sodium sulfite. A re-suspension supplemented no salts was also prepared as a comparative example.

The cell suspensions were preserved in the dark at 20° C. for 60 days. The amount of enzyme activity in 1 ml of each preserved cell suspension was measured in the same manner as described in Inventive Example 1. Table 2 shows relative values, with the amount of activity in 1 ml of each preserved cell suspension on day 0 defined as 1.0.

TABLE 2

| Kinds and Concentrations of Salts | | Days Stored | |
|---|---|---|---|
| | | 0 | 60 |
| no addition | | 1.0 | 0.2 |
| sodium sulfate | 300 mM | 1.0 | 0.9 |
| sodium chloride | 300 mM | 1.0 | 0.7 |
| potassium chloride | 300 mM | 1.0 | 0.7 |
| sodium sulfite | 100 mM | 1.0 | 0.6 |

INVENTIVE EXAMPLE 3

The cultured broth of Inventive Example 1 was dispensed in 20 ml portions in 3 centrifugation tubes and centrifuged (10,000 rpm, 15 minutes, 10° C.), and the thus collected cells in each tube were washed once with 20 ml of 300 mM phosphate buffer ($Na_2HPO_4$—$KH_2PO_4$) having a pH value of 6.0 (comparative example), 7.0 or 8.0 and re-suspended in 20 ml of the same phosphate buffer having the respective pH value used in the wash. These cell suspensions were preserved in the dark at 20° C. for 60 days. The amount of activity in 1 ml of each preserved cell suspension was measured in the same manner as described in Inventive Example 1. Table 3 shows relative enzyme activity values, with the amount of activity in 1 ml of each preserved cell suspension on day 0 defined as 1.0.

TABLE 3

| | Days Stored | |
|---|---|---|
| | 0 | 60 |
| pH 6.0 | 1.0 | 0.1 |
| pH 7.0 | 1.0 | 1.1 |
| pH 8.0 | 1.0 | 1.2 |

INVENTIVE EXAMPLE 4

(1) Culturing

Rhodococcus sp. HT40-6, which has nitrile hydratase activity, was cultured aerobically at 30° C. for 96 hours in the following medium supplemented with ε-caprolactam as an enzyme activity inducer.

Medium composition (pH 7.5):

| Glucose | 27 g |
|---|---|
| Polypeptone | 4 g |
| Yeast extract | 2 g |
| Disodium hydrogen phosphate | 7.1 g |
| Potassium dihydrogen phosphate | 6.8 g |
| Ammonium nitrate | 2 g |
| Magnesium chloride | 0.4 g |
| Ammonium sulfate | 0.2 g |
| Calcium chloride | 0.04 g |
| Manganese sulfate | 0.03 g |
| Cobalt chloride.$6H_2O$ | 0.03 g |
| Iron chloride | 0.006 g |
| Zinc sulfate | 0.003 g |
| ε-Caprolactam | 4 g |
| Distilled water | 1,000 ml |

(2) Preparation of Cell Suspension to be Preserved

The cultured broth was dispensed in 45 ml portions in 5 centrifugation tubes and centrifuged (10,000 rpm, 15 minutes, 10° C.), and the thus collected cells in each tube were washed once with 45 ml of 50 mM phosphate buffer (pH 8.0, $K_2HPO_4$—$KH_2PO_4$) (comparative example) or 300 mM phosphate buffer (pH 8.0, Na$_2$HPO$_4$—KH$_2$PO$_4$) and again suspended in 20 ml of the respective concentration of phosphate buffer used in the wash. The thus prepared cell suspensions were preserved in the dark at 20° C. for 120 days, and a portion of each cell suspension was sampled on day 0 and day 120 to measure the enzyme activity.

(3) Measurement of Nitrile Hydratase Activity

The reaction was carried out by the same procedure under the same conditions as described in Inventive Example 1, and the product formed (mandelamide) was quantitatively measured by liquid chromatography under the same conditions as described in Inventive Example 1

(4) Results

Table 4 shows relative enzyme activity values, with the amount of activity in 1 ml of each preserved cell suspension on day 0 defined as 1.0.

TABLE 4

|  |  | Days Stored | |
| --- | --- | --- | --- |
|  |  | 0 | 120 |
| K$_2$HPO$_4$/KH$_2$PO$_4$ | 50 mM | 1.0 | 0.0 |
| Na$_2$HPO$_4$/KH$_2$PO$_4$ | 50 mM | 1.0 | 0.0 |
| K$_2$HPO$_4$/KH$_2$PO$_4$ | 300 mM | 1.0 | 1.1 |
| Na$_2$HPO$_4$/KH$_2$PO$_4$ | 300 mM | 1.0 | 1.0 |

INVENTIVE EXAMPLE 5

*Gordona terrae* MA-1, *Rhodococcus* sp. HT40-6 and *Rhodococcus rhodochrous* ATCC 33278 were separately cultured in accordance with the methods of Inventive Example 1 for MA-1 and Inventive Example 4 for HT40-6 and ATCC 33278. A 20 ml portion of each of the thus cultured broths was centrifuged (10,000 rpm, 15 minutes, 10° C.), and the collected cells were washed once with the same volume of 100 mM borate buffer (pH 9.0, Na$_2$B$_4$O$_7$.10H$_2$O—HCl) and re-suspended in 20 ml of the same buffer. The cell suspensions were preserved in the dark at 20° C. for 200 days, and the amount of activity in 1 ml of each of the preserved cell suspension on day 0 and day 200 was measured in accordance with the respective methods of Inventive Examples 1 and 4. Table 5 shows relative values, with the amount of activity in 1 ml of each preserved cell suspension on day 0 defined as 1.0.

TABLE 5

|  | Days Stored | |
| --- | --- | --- |
| Strain | 0 | 200 |
| MA-1 | 1.0 | 0.9 |
| HT40-1 | 1.0 | 0.8 |
| ATCC 33278 | 1.0 | 0.8 |

INVENTIVE EXAMPLE 6

(1) Preparation of Immobilized Cell in Particles

*Rhodococcus rhodochrous* J-1, which have nitrile hydratase activity, was aerobically cultured in a medium (pH 7.0) containing 2% glucose, 1% urea, 0.5% peptone, 0.3% yeast extract and 0.05% cobalt chloride (all % by weight). The resulting cells were washed with 50 mM phosphate buffer (pH 7.0). Then, 500 g of a monomer mixture of 20% by weight acrylamide, 2% by weight methylene bisacrylamide and 2% by weight 2-dimethylaminopropyl methacrylamide was added to 500 g of the cell suspension (20% by weight on a dry cell basis) and thoroughly suspended. To this was added 2 g of 50% by weight ammonium persulfate and 2 g of 50% by weight N,N,N',N'-tetramethylethylenediamine to cause polymerization and gelation. The resulting gel was cut into cubes of about 1 mm square, which were washed 5 times with 1,000 ml of 20 mM sodium sulfate to obtain immobilized cells in particles.

(2) Preparation of an Immobilized Cell Particle Suspension to be Preserved

A 200 ml portion of immobilized cells in particles, which were precipitated by standing, was put into a 500 ml capacity polyethylene container, mixed with 200 ml of 40% ammonium sulfate solution (adjusted to pH 7.0) and 8% sodium chloride solution (adjusted to pH 7.0) respectively, and then preserved at 30° C. for 100 days. The same procedure was repeated except that 20 mM of sodium sulfate was added (comparative example).

(3) Measurement of Nitrile Hydratase Activity

A small portion of the thus preserved immobilized cell particle suspension was washed with 5 volumes of 50 mM phosphate buffer (pH 7.0, Na$_2$HPO$_4$—KH$_2$PO$_4$). The samples were then wrapped in gauze and dehydrated by centrifugation, and about 1 g of the thus treated particles were suspended in 100 ml of the same phosphate buffer. The suspension was mixed with 5% acrylonitrile solution in the same phosphate buffer, and the reaction was begun by shaking at 0° C. for 20 minutes. The reaction was terminated by filtering the reaction mixture through a 0.45 µm filter. The amount of the acrylamide formed in the resulting filtrate was analyzed by gas chromatography (injection temp., 220° C.; column temp., 180° C.; packing, Porapack PS 80-100MESH (manufactured by Waters); detector, FID).

(4) Results

Table 6 shows relative enzyme activity values, with the amount of activity in 1 g of immobilized cells in particles on day 0 defined as 1.0.

TABLE 6

|  | Days Stored | |
| --- | --- | --- |
|  | 0 | 100 |
| 20 mM sodium sulfate | 1.0 | 0.6 |
| 20% ammonium sulfate | 1.0 | 0.9 |
| 4% sodium chloride | 1.0 | 0.8 |

Thus, the present invention provides an industrially useful method, for preserving a large quantity of cells or immobilized cells in particles having nitrile hydratase or nitrilase enzyme activity for a prolonged period of time (e.g., 300 days) without cell lysis or enzyme deterioration even at room temperature. The present invention also renders possible a sharp reduction in labor and cooling costs, which are necessary in the conventional preservation process.

While the invention has been described in detail and with reference to specific embodiments thereof, it will be apparent to one skilled in the art that various changes and modifications can be made therein without departing from the spirit and scope thereof.

What is claimed is:

1. A method for stably preserving microbial cells having nitrile hydratase or nitrilase activity, and the nitrile hydratase or nitrilase activity thereof, for a prolonged period of time, comprising preserving said cells as a suspension of the microbial cells or as a suspension of cells immobilized in particles in an aqueous medium, wherein said aqueous medium consists of a neutral or weakly basic aqueous solution of inorganic salts, having a molarity ranging from 100 mM to the saturation concentration of said inorganic salts.

2. The method according to claim 1, wherein said aqueous solution of inorganic salts is an aqueous solution of at least one salt selected from the group consisting of phosphates, borates, sulfates, sulfites and hydrochlorides.

3. The method according to claim 1, wherein said inorganic salts are at least one selected from the group consisting of sodium salts, potassium salts and ammonium salts.

4. The method according to claim 1, wherein said aqueous solution of inorganic salts has a pH value ranging from pH 7 to 10.

5. The method according to claim 1, wherein said microbial cells are *Gordona terrae* MA-1 (FERM BP-4535).

6. The method according to claim 1, wherein said microbial cells are *Rhodococcus rhodochrous* sp. HT40-6 (FERM BP-5231).

7. The method according to claim 1, wherein said microbial cells are *Rhodococcus rhodochrous* J-1 (FERM BP-1478).

8. The method according to claim 1, wherein said microbial cells are *Rhodococcus rhodochrous* ATCC 33278.

9. The method according to claim 1, wherein said concentration of said cells immobilized in particles ranges from 0.1 to 30% by weight on a dry cell basis.

10. The method according to claim 1, having a preservation temperature ranging from 0° to 40° C.

11. The method according to claim 1, wherein said aqueous solution of inorganic salts comprises a phosphate buffer having a molarity ranging from 300–700 mM.

12. The method according to claim 1, wherein said aqueous solution of inorganic salts comprises a phosphate buffer having a molarity of 50 mM and a sodium sulfate solution having a molarity of 300 mM.

13. The method according to claim 1, wherein said cells immobilized in particles are suspended in an ammonium sulfate aqueous solution.

* * * * *